United States Patent [19]
Kawase

[11] Patent Number: 5,895,625
[45] Date of Patent: Apr. 20, 1999

[54] FUNERAL DEODORANT

[76] Inventor: Ituko Kawase, 2226-1, Yamamiya, Fujinomiya-shi, Shizuoka-ken, Japan

[21] Appl. No.: 08/781,514

[22] Filed: Jan. 9, 1997

[30] Foreign Application Priority Data

Jul. 31, 1996 [JP] Japan ................ 8-217809

[51] Int. Cl.$^6$ .............. A01N 1/00; A01N 65/00; A61L 9/01
[52] U.S. Cl. .............. 422/5; 424/75; 424/76.21; 424/76.9; 424/195.1
[58] Field of Search .............. 422/5; 424/195.1, 424/75, 76.21, 76.9

[56] References Cited

U.S. PATENT DOCUMENTS

| | | |
|---|---|---|
| 4,151,630 | 5/1979 | Havey . |
| 4,308,293 | 12/1981 | Tribble et al. . |
| 5,024,731 | 6/1991 | Nagata et al. .............. 203/99 |

FOREIGN PATENT DOCUMENTS

| | | |
|---|---|---|
| 5-310522 | 11/1993 | Japan . |
| 6-7398 | 1/1994 | Japan . |
| 6-23027 | 2/1994 | Japan . |
| 7-124206 | 5/1995 | Japan . |
| 7-300769 | 11/1995 | Japan . |

*Primary Examiner*—Krisanne Thornton
*Assistant Examiner*—E. Leigh McKane
*Attorney, Agent, or Firm*—Birch, Stewart, Kolasch and Birch, LLP

[57] ABSTRACT

A funeral deodorant comprising an active deodorant component obtained from pyroligneous liquid is applied to a dead body for preventing and masking odors therefrom.

4 Claims, No Drawings

FUNERAL DEODORANT

This invention relates to a funeral deodorant and more particularly, to a deodorant for destroying or masking odors from corpses.

BACKGROUND OF THE INVENTION

For the past decades, a coffin is filled with dry ice to prevent a corpse from giving off odors before the body is cremated or buried. Full deodorization is difficult with dry ice.

An object of the present invention is to provide a funeral deodorant for destroying or masking odors from a dead body until the body is cremated or buried.

SUMMARY OF THE INVENTION

The present invention which achieves the above object provides a funeral deodorant comprising an active deodorant component obtained from pyroligneous liquid.

It has been found that an active deodorant component obtained from pyroligneous acid or liquid is not only effective for fully destroying or masking odors from a dead body, but also has an antiseptic (decay preventing or retarding) action and even a bactericidal action.

Although the deodorizing mechanism is not well understood and the invention is not bound to the theory, it is believed that acetic acid and other organic acids contained in the active deodorant component obtained from pyroligneous liquid neutralize alkaline smelling substances such as ammonia and sulfur compounds and mask offensive odors.

DETAILED DESCRIPTION OF THE INVENTION

According to the invention, an active deodorant component is obtained from pyroligneous liquid or wood vinegar. The pyroligneous liquid used herein may be selected from known ones obtained by the destructive distillation of wood. The type of wood as a source of pyroligneous liquid and the method of collection or extraction are not critical. For example, pyroligneous liquid may be derived by heating pieces of wood or bark of oak, chinquiapin, cherry and beech, for example, at 170 to 180° C. for carbonization to generate water-containing smoke, cooling the smoke, and collecting the condensed liquid. Preferably the thus obtained pyroligneous liquid is subject to centrifugal separation or aged for 2 to 3 months whereby tar and solid impurities are separated or settled out, collecting a supernatant.

As the active deodorant component obtained from pyroligneous liquid, the pyroligneous liquid as such may be used. One preferred form of pyroligneous liquid is a purified product, which is typically obtained by removing a low-boiling fraction containing methanol, formaldehyde and tar from the pyroligneous liquid. In one preferred embodiment, pyroligneous liquid is distilled to collect a fraction at 95 to 105° C., especially 98 to 103° C. A solid or particulate product may be obtained from this liquid fraction by freeze drying or spray drying. These liquid fraction and solid or particulate product are advantageous to use since they are substantially free of low-boiling components such as methanol and formaldehyde and harmful components such as 3,4-benzpyrene and have a fully deodorant action. The invention is not limited to these forms and any form of pyroligneous liquid from which low-boiling volatile components and harmful components such as 3,4-benzpyrene have been removed is useful.

The active deodorant component obtained from pyroligneous liquid may be used as such. Preferably the liquid fraction obtained by further distillation of pyroligneous liquid as described above is used by adsorbing or supporting on carriers such as cyclodextrin, starch, powdered grains and potatoes (e.g., corn, potato and sweet potato), silica and active carbon or absorbing in cotton wadding. In addition to the above-mentioned solid or particulate product, a powdery or gel-like product obtained from the liquid fraction by removing the majority of water is also useful and they may be used by melting at about 200° C. and spraying, adsorbing or supporting on similar carriers.

The liquid fraction may be diluted by ethanol at a concentration of 5% by weight or more, preferably 10% by weight or more. The deodorant comprising an active deodorant component obtained from pyroligneous liquid may be used in admixture with another deodorant.

The deodorant of the invention may be used by placing it near the dead body, typically in a coffin. Preferably the deodorant is directly applied to the dead body as by spraying. Alternatively, cotton wadding having the deodorant absorbed therein may be inserted into the dead body. Such direct application permits the deodorant to exert more deodorant and antiseptic actions for suppressing generation of odors and retarding decay and discoloration. The deodorant of the invention may be used in combination with conventional dry ice. However, the deodorant of the invention ensures sufficient deodorant and antiseptic actions when the amount of dry ice is reduced or even in the absence of dry ice.

An experimental example is described below.

EXPERIMENT

Pyroligneous liquid was aged to allow tar and solid impurities to settle down. After the precipitate was removed, the supernatant was heated for distillation. A fraction obtained up to 98° C. was discarded and a fraction collected at a temperature of 98 to 103° C. was cooled into a liquid. The liquid was prepared into four forms of deodorant. (1) The liquid was adsorbed in silica. (2) The liquid was spray dried into a particulate product. (3) The particulate product or a gel-like product obtained from the liquid by removing about 90% of water was melted at 200° C. and then adsorbed in cyclodextrin. (4) The liquid was absorbed in cotton wadding.

The deodorant was used by directly applying it to a dead body or inserting the cotton wadding into nostrils. For two days in summer until cremation, little odors were perceivable.

There has been described a deodorant which is effective for preventing and masking offensive odors from a dead body.

What is claimed is:

1. A method for neutralizing odors from a dead body comprising placing near said body a deodorant comprising a fraction distilled from a pyroligneous liquid and collected at 95 to 105° C. absorbed on a solid carrier, wherein said fraction is first treated to remove the majority of the water therefrom to form a powder or gel and said powder or gel is then melted and absorbed on said solid carrier.

2. The method of claim 1, wherein said solid carrier is selected from the group consisting of cyclodextrin, starch, powdered grains, potatoes, silica, active carbon and cotton wadding.

3. The method of claim 1, wherein said deodorant is placed near said body in the absence of dry ice.

4. A method for neutralizing odors from a dead body comprising:

distilling pyroligneous liquid and collecting a fraction at 95 to 105° C.;

removing a majority of water from said fraction to produce a powder or a gel;

melting said powder or gel to produce a deodorant;

absorbing said deodorant on a solid carrier; and placing said solid carrier and deodorant near the dead body, wherein the deodorant neutralizes odors produced by the dead body.

* * * * *